(12) United States Patent
Raby et al.

(10) Patent No.: US 7,354,268 B2
(45) Date of Patent: Apr. 8, 2008

(54) MOVEMENT OF ORTHODONTIC OBJECTS ALONG A VIRTUAL ARCHWIRE WITHIN A THREE-DIMENSIONAL (3D) ENVIRONMENT

(75) Inventors: Richard E. Raby, North St. Paul, MN (US); Nicholas A. Stark, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 710 days.

(21) Appl. No.: 10/959,625

(22) Filed: Oct. 6, 2004

(65) Prior Publication Data

US 2006/0073436 A1 Apr. 6, 2006

(51) Int. Cl.
*A61C 3/00* (2006.01)

(52) U.S. Cl. .................................. 433/24; 433/215

(58) Field of Classification Search ................. 433/24, 433/215
See application file for complete search history.

(56) References Cited

U.S. PATENT DOCUMENTS

| | | | |
|---|---|---|---|
| 5,879,158 | A | 3/1999 | Doyle et al. |
| 6,099,314 | A | 8/2000 | Kopelman et al. |
| 6,123,544 | A | 9/2000 | Cleary |
| 6,152,731 | A | 11/2000 | Jordan et al. |
| 6,318,994 | B1 | 11/2001 | Chishti et al. |
| 6,322,359 | B1 | 11/2001 | Jordan et al. |
| 6,334,772 | B1 | 1/2002 | Taub et al. |
| 6,334,853 | B1 | 1/2002 | Kopelman et al. |
| 6,457,978 | B1 | 10/2002 | Cloonan et al. |
| 6,632,089 | B2 | 10/2003 | Rubbert et al. |
| 6,664,986 | B1 | 12/2003 | Kopelman et al. |
| 6,695,613 | B2 | 2/2004 | Taub et al. |
| 6,697,164 | B1 | 2/2004 | Babayoff et al. |
| 6,739,869 | B1 | 5/2004 | Taub et al. |
| 7,029,275 | B2 | 4/2006 | Rubbert et al. |
| 7,033,327 | B2 | 4/2006 | Raby |
| 7,080,979 | B2 | 7/2006 | Rubbert et al. |

(Continued)

FOREIGN PATENT DOCUMENTS

WO 97/03622 2/1997

OTHER PUBLICATIONS

U.S. Appl. No. 10/734,323, "Method of Placing Orthodontic Brackets on Teeth in a 3D Virtual World," filed Dec. 12, 2003.

(Continued)

*Primary Examiner*—Cris Rodriguez
*Assistant Examiner*—Candice C Stokes
(74) *Attorney, Agent, or Firm*—James D. Christoff

(57) ABSTRACT

Techniques are described for moving an orthodontic object (e.g., an orthodontic appliance and/or its associated tooth) in response to input indicative of a desired movement of the object along a virtual archwire. The movement of objects along the archwire may be used to generate a three-dimensional (3D) representation of a patient's dental arch. The manner in which the object is to be moved along the virtual archwire may be determined automatically during creation of a treatment plan for a patient, or may be determined and input by an orthodontic practitioner as part of the creation of the treatment plan.

45 Claims, 11 Drawing Sheets

U.S. PATENT DOCUMENTS

| | | |
|---|---|---|
| 2002/0150859 A1 | 10/2002 | Imgrund et al. |
| 2003/0003416 A1 | 1/2003 | Chishti et al. |
| 2003/0163291 A1 | 8/2003 | Jordan et al. |
| 2003/0215764 A1 | 11/2003 | Kopelman et al. |
| 2003/0219692 A1 | 11/2003 | Kopelman et al. |
| 2003/0224316 A1 | 12/2003 | Marshall |
| 2004/0054304 A1 | 3/2004 | Raby |
| 2004/0142297 A1 | 7/2004 | Taub et al. |
| 2004/0142298 A1 | 7/2004 | Taub et al. |
| 2005/0191593 A1 | 9/2005 | Knopp |

OTHER PUBLICATIONS

U.S. Appl. No. 10/771,641, "Planar Guides to Visually Aid Orthodontic Appliance Placement with a Three-Dimensional (3D) Environment," filed Feb. 4, 2004.

U.S. Appl. No. 10/903,686, "Automatic Adjustment of an Orthodontic Bracket to a Desired Occlusal Height Within a Three-Dimensional (3D) Environment," filed Jul. 30, 2004.

U.S. Appl. No. 10/959,624, "Placing Orthodontic Objects Along an Archwire Within a Three-Dimensional (3D) Environment", filed Oct. 6, 2004.

MOVEMENT OF ORTHODONTIC OBJECTS ALONG A VIRTUAL ARCHWIRE WITHIN A THREE-DIMENSIONAL (3D) ENVIRONMENT

TECHNICAL FIELD

The invention relates to electronic orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets that are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each bracket in the exact proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal direction, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, in a technique known as indirect bonding, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the invention is directed to techniques for moving an orthodontic object (e.g., an orthodontic appliance and/or its associated tooth) to a specified position along a virtual archwire. The movement of orthodontic objects along the archwire may be used to generate a three-dimensional (3D) representation of a patient's dental arch. The manner in which the object is to be moved along the virtual archwire may be determined automatically during creation of a treatment plan for a patient, or may be determined and input by an orthodontic practitioner as part of the creation of the treatment plan.

In one embodiment, the invention is directed to a method comprising representing an archwire within a three-dimensional (3D) environment with a plurality of segments, receiving input indicative of movement of an orthodontic object along the archwire, and moving the orthodontic object within the 3D environment as indicated along the archwire based on the plurality of segments.

In another embodiment, the invention is directed to a system comprising a computing device and modeling software executing on the computing device, wherein the modeling software comprises an object movement control module that represents an archwire within a three-dimensional (3D) environment with a plurality of segments, receives input indicative of movement of an orthodontic object along the archwire, and moves the orthodontic object as indicated along the archwire based on the plurality of segments.

In another embodiment, the invention is directed to a computer-readable medium containing instructions. The instructions cause a programmable processor to represent an archwire within a three-dimensional (3D) environment with a plurality of segments, receive input indicative of movement of an orthodontic object along the archwire, and move the orthodontic object as indicated along the archwire based on the plurality of segments.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
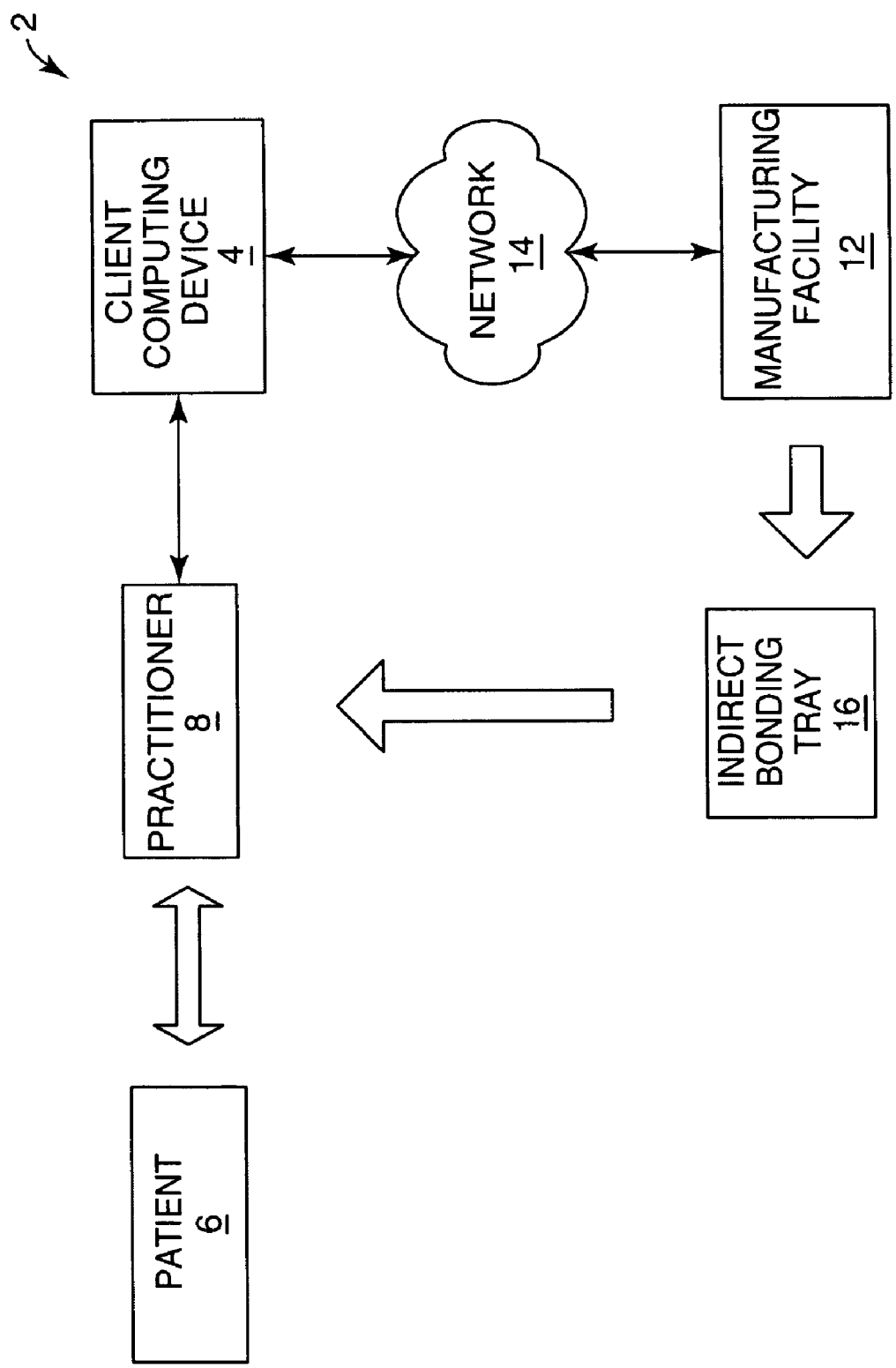
FIG. 1 is a block diagram illustrating an exemplary computer environment in which a client computing device moves orthodontic appliances along an archwire.

FIG. 1 is a block diagram illustrating an exemplary computer environment 2 in which a client computing device 4 presents an environment for moving an orthodontic object, such as an orthodontic appliance and/or its associated tooth, in response to inputs indicative of desired movements along a virtual archwire. The positions of the orthodontic objects along the archwire may be used to generate a three-dimensional (3D) representation of a patient's dental arch. The movements of the orthodontic object may be determined automatically by client computing device 4 during creation of a treatment plan for a patient, or may be determined and input by practitioner 8. The client computing device 4 may also display a 3D representation of the orthodontic objects to allow the practitioner to visualize the result.

The 3D representation of the dental arch may be initially generated by digitally scanning a physical dental impression of the teeth of patient 6, or by scanning a casting made from the impression. Alternatively, practitioner 8 may use an intraoral scanner to produce the 3D digital representation directly from the teeth of patient 6. Other methods of scanning are also possible. Practitioner 8 may interact with client computing device 2 to view the 3D digital representation of the teeth and define a proposed orthodontic prescription by selecting virtual brackets that embody certain geometric attributes, then precisely positioning those brackets on individual teeth within the modeled dental arch. During this process, the modeling software manipulates each bracket and each tooth as a separate object within the 3D environment, and fixes the position of each bracket within the 3D space relative to a coordinate system associated with the bracket's respective tooth. Consequently, practitioner 8 is able to independently view and precisely locate each bracket within the 3D environment relative to its respective tooth.

Once a proposed orthodontic prescription is determined, the brackets are placed and displayed and the practitioner has indicated his or her approval, client computing device 4 communicates the bracket placement positions to manufacturing facility 12 via network 14. In response, manufacturing facility constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Although the description will generally discuss the display and positioning of orthodontic brackets, it shall be understood that client computing device 4 may display and/or position any type of orthodontic appliance without departing from the scope of the present invention. Examples of such orthodontic appliances include orthodontic brackets, buccal tubes, sheaths or buttons. In addition, client computing device 4 need not display a full visual representation of the appliance. Rather, a portion of the appliance may be displayed. As another alternative, client computing device 4 need not display the appliance itself. Rather, another object associated with an appliance or with the placement of an appliance may be shown instead of or in addition to the appliance itself. Examples of such other objects include crosshairs (intersecting lines indicating the position on a tooth where the center of an appliance is to be placed), placement jigs, placement guides, or other peripheral which may represent or be attached to an appliance, or which may be otherwise associated with an appliance and/or its placement. The terms "appliance" or "bracket" as used herein shall therefore be understood to include any type of appliance, a full or partial representation of an appliance, or any object associated with an appliance and/or its placement.

Figure 2:
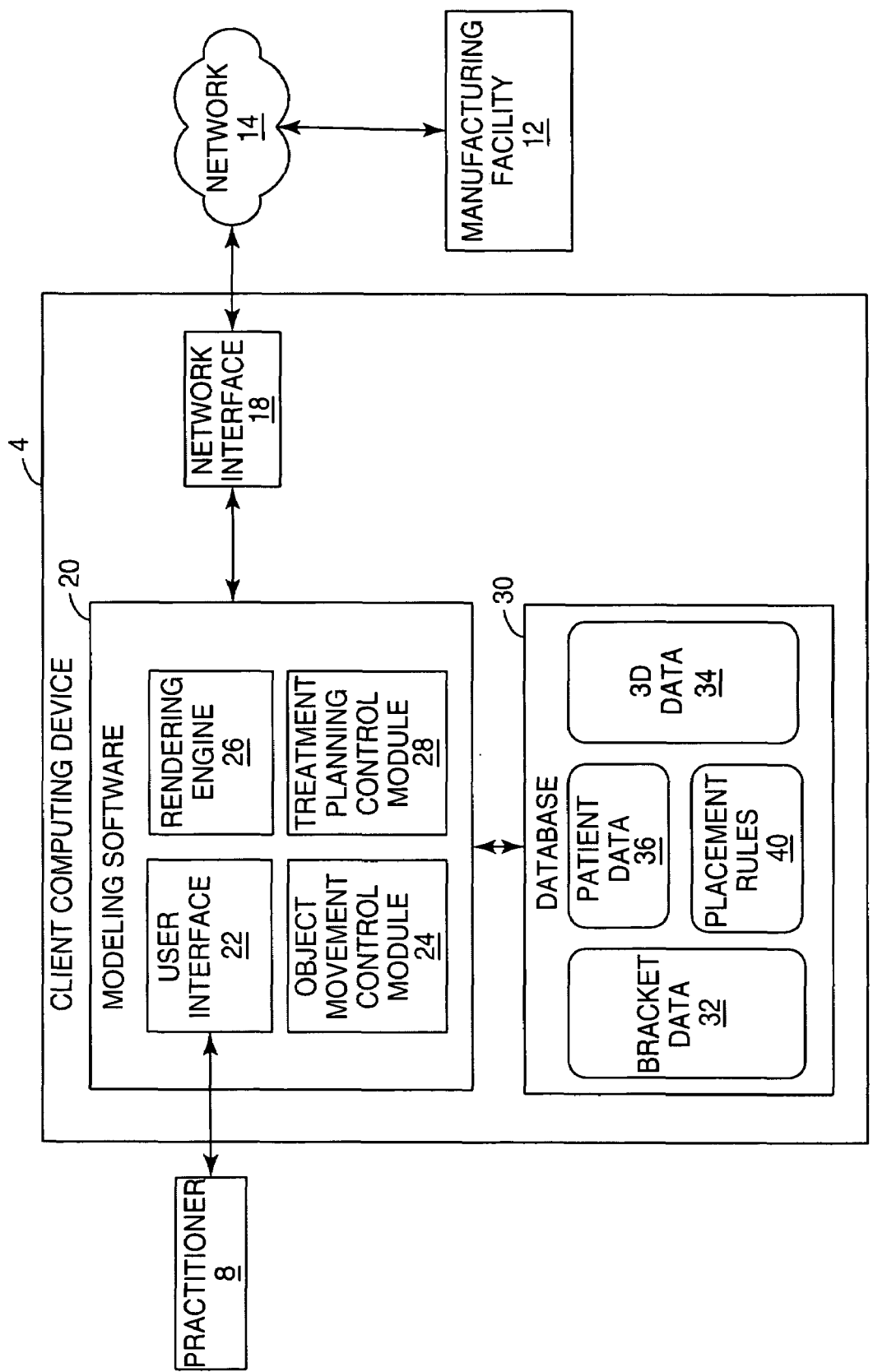
FIG. 2 is a block diagram illustrating an example embodiment of the client computing device of FIG. 1 in further detail.

FIG. 2 is a block diagram illustrating an example embodiment of client computing device 4 in further detail. In the illustrated embodiment, client computing device 4 provides an operating environment for modeling software 20. As described above, modeling software 20 presents a modeling environment for modeling and depicting the 3D representation of the teeth of patient 6 (FIG. 1). In the illustrated embodiment, modeling software 20 includes a user interface 22, an object movement control module 24, treatment planning control module 28 and a rendering engine 26.

User interface 22 provides a graphical user interface (GUI) that visually displays the 3D representation of the patient's teeth as well as 3D representations of the brackets. In addition, user interface 22 provides an interface for receiving input from practitioner 8, e.g., via a keyboard and a pointing device, for manipulating the orthodontic objects and placing or moving the brackets on respective teeth within the modeled dental arch. User interface 22 may also visually display a 3D representation of the patient's dental arch and/or of specified portions of the patient's dental arch.

Treatment planning control module 28 can be considered an interactive module for development of an orthodontic treatment plan. When movements of an orthodontic object, such as a bracket or tooth, along an archwire are indicated, treatment planning control module interacts with object movement control module 24 to move the virtual representation of the orthodontic object as indicated along the virtual archwire.

Because each orthodontic object such as a bracket and a tooth are separate and independent virtual objects, they can be moved freely relative to each other, for example to selectively position each virtual bracket on its respective virtual tooth. Treatment planning control module 28 may allow practitioner 8 to interactively position any of the orthodontic objects along any combination of X, Y and Z directions, as well as interactively rotate each orthodontic object about the X, Y and Z axes. Practitioner 8 may select an individual orthodontic object for movement by, for example, clicking on a particular bracket, tooth or other orthodontic object, selecting a bracket number or tooth number from a drop-down or other menu, or by any other suitable means of selecting an object. User interface 22 may include navigational controls for moving and/or positioning the orthodontic object, such as by clicking on an icon that displays navigational controls for moving the virtual orthodontic objects. User interface 22 may also allow the user to move individual orthodontic objects independently of each other. For example, practitioner 8 may be able to specify whether brackets and their associated teeth should move independently of each other. Alternatively, user interface 22 may allow the user to move orthodontic objects together, if desired, for example, by moving a tooth along with its associated bracket or vice versa. The result is that the client computing device 4 allows the orthodontist to interactively create a treatment plan for a patient by selecting brackets for each tooth and precisely positioning the placement of the virtual brackets on the teeth.

Object movement control module 24 seamlessly moves orthodontic objects, such as appliances and/or their associated teeth, in response to inputs indicative of desired movements along a virtual archwire. The manner in which a particular orthodontic object is moved along the archwire may be determined by treatment planning control module 28 or may be input by the practitioner 8 via user interface 22. In one embodiment, object movement control module 24 moves orthodontic objects along the archwire using the straight-wire concept. However, it shall be understood that methods other than the straight wire concept could also be used, and that the invention is not limited in this respect. A digital representation of the patient's dental arch may be displayed on user interface 22.

Modeling software 20 interacts with database 30 to access a variety of data, such as bracket data 32, 3D data 34, patient data 36, and placement rules 40. Database 30 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS), object relational (OR-DBMS) or other type of database management system. The data may, for example, be stored within a single relational database such as SQL Server from Microsoft Corporation. Although illustrated as local to client computing device 4, database 30 may be located remote from the client computing device 4 and coupled to the client computing device 4 via a public or private network, e.g., network 14.

Bracket data 32 describes a set of commercially available brackets or other orthodontic appliances that may be selected by practitioner 8 and positioned within the 3D modeling environment. For example, bracket data 32 may store a variety of attributes for the commercially available brackets, such as dimensions, slot locations and characteristics, torque angles, angulations and other attributes. User interface 22 provides a menu-driven interface by which practitioner 8 selects the type of brackets for use in defining an orthodontic prescription for patient 6.

Patient data 36 describes a set of one or more patients, e.g., patient 6, associated with practitioner 8. For example, patient data 36 specifies general information, such as a name, birth date, and a dental history, for each patient. In addition, patient data 36 specifies a current prescription specified for each of the patients, including the types of brackets selected by practitioner 8 for use with each of the patients, and their associated positions and orientations on the teeth of patient 6.

The orthodontic industry has developed standard prescriptions for many commercially available orthodontic appliances. These standardized prescriptions generally tend to satisfy the functional and the aesthetic requirements for most patients. The standardized prescriptions may be used to achieve uniformity among patients or to avoid the more time consuming process of devising a custom set of metrics for each individual patient.

For some patients, a standardized set of metrics for the teeth in the dentition may be satisfactory. For other patients, practitioner 8 may desire to create a customized prescription to achieve a more aesthetically pleasing result, or to more adequately take into account that patient's malocclusion. As another example, a combination of standardized and customized prescriptions for different teeth in the dentition may be used. Practitioner 8 inputs the desired prescription via user interface 22, which is then stored in database 30 as patient data 36.

Placement rules 40 may specify industry-defined placement rules for commercially available appliances. In addition, placement rules 40 may include user-defined rules specified by practitioner 8 or other rules for controlling appliance placement. For example, one rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a base of the bracket on the FACC of the tooth equidistant from the occlusal edge or occlusal-most point on the FACC and the gingival margin of the crown. This location is also known as the Facial Axis Point (FA Point). As another example, practitioner 8 may desire to place brackets at a position that is different from the FA Point. Consequently, practitioner 8 may specify different prescriptions for different types of teeth in the dentition, for different types of brackets, or both. Optionally, the prescription may be based in whole or in part on known rules associated with a particular type of the appliances selected by practitioner 8.

Rendering engine 26 accesses and renders 3D data 34 to generate the 3D view presented to practitioner 8 by user interface 22. More specifically, 3D data 34 includes information defining the 3D objects that represent each tooth and appliance within the 3D environment. Rendering engine 26 processes each object to render a 3D triangular mesh based on viewing perspective of practitioner 8 within the 3D environment. User interface 22 displays the rendered 3D triangular mesh to practitioner 8, and allows the practitioner to change viewing perspectives and manipulate objects within the 3D environment. Orthodontic appliances, or brackets as they will generally be referred to herein, may initially be placed in the 3D environment using any of several different methods. For example, the brackets may initially be placed in the 3D environment using the method described in copending and commonly assigned U.S. patent application Ser. No. 10/734,323, entitled "Method of Placing Orthodontic Brackets on Teeth in a 3D Virtual World", filed Dec. 12, 2003 to Raby, et al., which is incorporated herein by reference in its entirety. Manual adjustment of orthodontic brackets may be assisted by use of visual planar guides, as described in copending and commonly assigned U.S. patent application Ser. No. 10/771,641, entitled "Planar Guides to Visually Aid Orthodontic Appliance Placement within a Three-Dimensional (3D) Environment", filed Feb. 4, 2004 to Raby, et al., which is incorporated herein by reference in its entirety. In that application, a system visually aids the user in manual placement of brackets through manual adjustments to bracket position and orientation. Other methods of placing or adjusting the position of brackets on the teeth may also be used. For example, a system for automatic adjustment of an orthodontic appliance to a desired occlusal height is described in copending and commonly assigned U.S. patent application Ser. No. 10/903,686, entitled "Automatic Adjustment of an Orthodontic Bracket to a Desired Occlusal Height Within a Three-Dimensional (3D) Environment", filed Jul. 30, 2004 to Raby, et al., which is incorporated herein by reference in its entirety. A system for placing teeth and/or brackets along an archwire is described in copending and commonly assigned U.S. patent application Ser. No. 10/959,624 "Placing Orthodontic Objects Along An Archwire within a Three-Dimensional (3D) Environment", filed on even date herewith to Raby, et al. which is incorporated herein by reference in its entirety.

It shall be understood that these and/or any other techniques may be used to initially place the orthodontic appliances on the teeth in the 3D environment and thus determine the patient's prescription, and that the invention is not limited in this respect. Moreover, although described for purposes of illustration with respect to modeling software 20 executing on client computing device 4, the techniques may be applied by any computing device, including servers remote from practitioner 8.

Figure 3A:
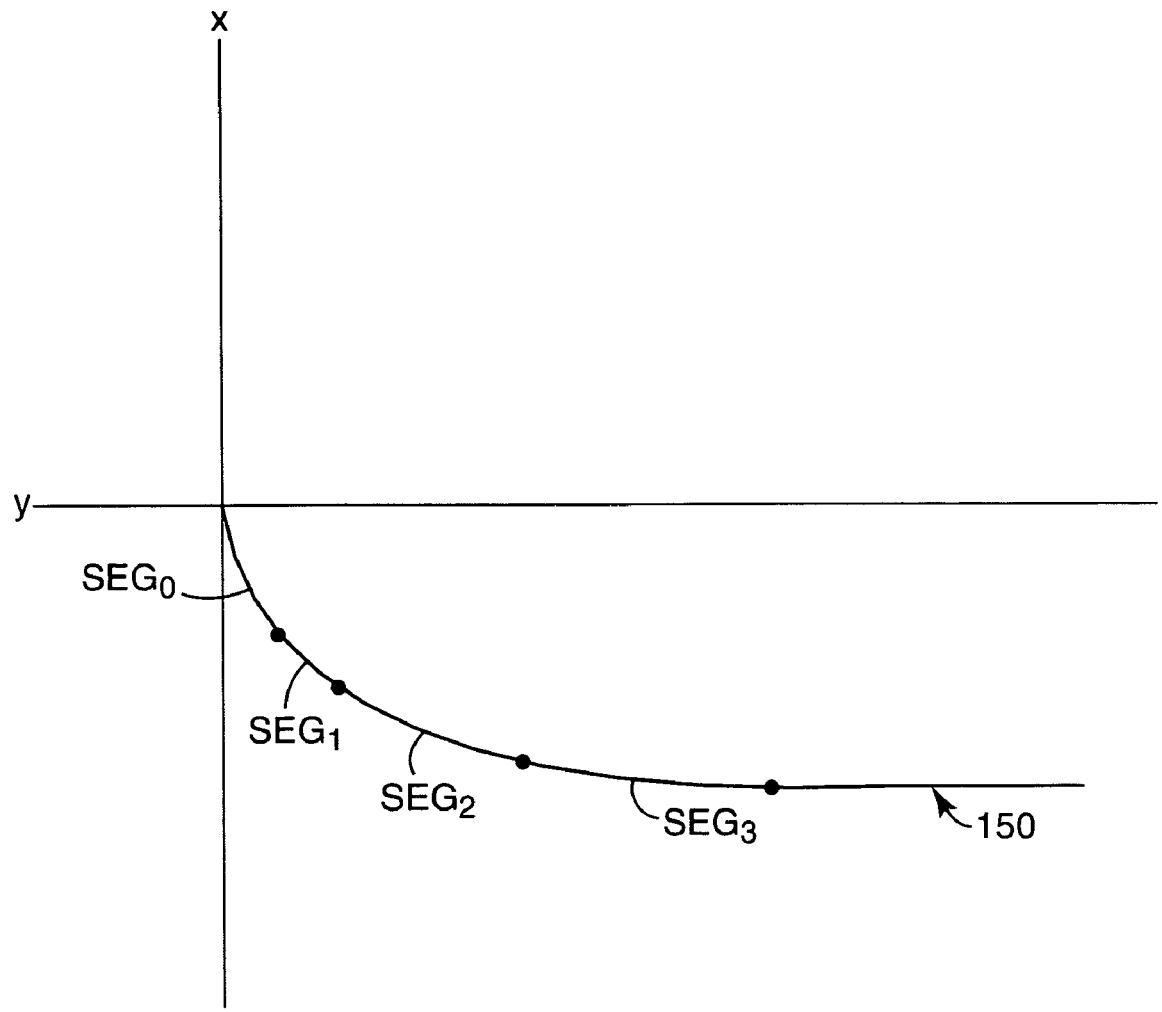
FIGS. 3A, 3B and 3C illustrate an exemplary virtual archwire defined by a series of arcs.

FIG. 3A is a diagram illustrating an exemplary virtual representation of one half of an archwire 150. As illustrated in FIG. 3A, modeling software 20 (FIG. 2) stores data that defines archwire 150 in the 3D virtual environment as a series of segments, $SEG_i$. In the example of FIG. 3A, there are four segments, referred to as $SEG_0 \ldots SEG_3$. However, it shall be understood that more or fewer segments could be used to represent archwire 150, and the invention is not limited in this respect.

Modeling software 20 represents each segment $SEG_i$ with a geometric relationship. The geometric relationships that represent the segments may be linear or nonlinear. Examples of linear relationships may include lines, line segments, a series of polylines or any other linear geometric relationships. Examples of nonlinear relationships may include circular curves, parabolic curves, elliptical curves, catenary curves, or any other type of nonlinear geometric relationship. Furthermore, the segments $SEG_i$ may also be represented by other higher order geometric relationships, such as parametric cubic curve segments, cubic splines, or any other higher order geometric relationship or relationship with multiple bends.

In one embodiment, all of the segments $SEG_i$ that represents a portion of the archwire may be represented by the same type of geometric relationship. For example, all of the segments $SEG_i$ may be represented by a circular curve. Alternatively, each segment may be represented by a different geometric relationship than the other segments. For example, $SEG_0$ may be a circular curve, $SEG_1$ may be a parabolic curve, $SEG_2$ may be a catenary curve, etc. In addition, the archwire 150 need not be represented by planar segments. Instead, the segments may bend in three dimensions if desired to more accurately represent a patient's dental arch.

In addition, each segment $SEG_i$ need not be smooth and continuous. For example each segment $SEG_i$ may be represented by a series of polylines (line segments), or by some other means of approximating or representing the shape of archwire 150. In one embodiment, the system may store a library of standardized archwires in database 30. Such standardized archwires may be designed to provide acceptable representations of the dental arches across a wide sample of the population. In another embodiment, a virtual archwire may be customized to a particular patient's dental arch. In that embodiment, the segments $SEG_i$ may be chosen which best fit each patient's dental arch. Alternatively, the patient's dental arch may be represented by a series of polylines which best fit the patient's dental arch. The standardized or customized virtual archwire may also be stored in database 30 (FIG. 2).

Modeling software 20 may define and display the virtual representation of archwire 150 to allow continuous movement of an appliance and/or a tooth from one segment to an adjacent segment as the appliance and/or tooth is moved along archwire 150. That is, modeling software 20 may define archwire 150 so that each segment $SEG_i$ shares a boundary (i.e., an end point) with each of adjacent segment $SEG_{i-1}$ and $SEG_{i+1}$. Object movement control module 24 may thus continuously move an appliance and/or a tooth along archwire 150 in a manner that is constrained by the geometric definitions of the segments.

Thus, it shall be understood that archwire 150 may be represented by a plurality of segments $SEG_i$, and that each segment $SEG_i$ may be represented by virtually any geometric relationship, may bend in one, two or three dimensions, or may be represented by a straight line or series of connected lines. The invention is therefore not limited with respect to the mathematical relationships that describe any of the segments, $SEG_i$. In one embodiment, the segments $SEG_j$ represent the center of the virtual archwire. In other embodiments, the segments $SEG_i$ may represent the labial side or the lingual side of the virtual archwire, or combinations thereof. It shall be understood, therefore, that the invention is not limited in this respect.

Figure 3B:
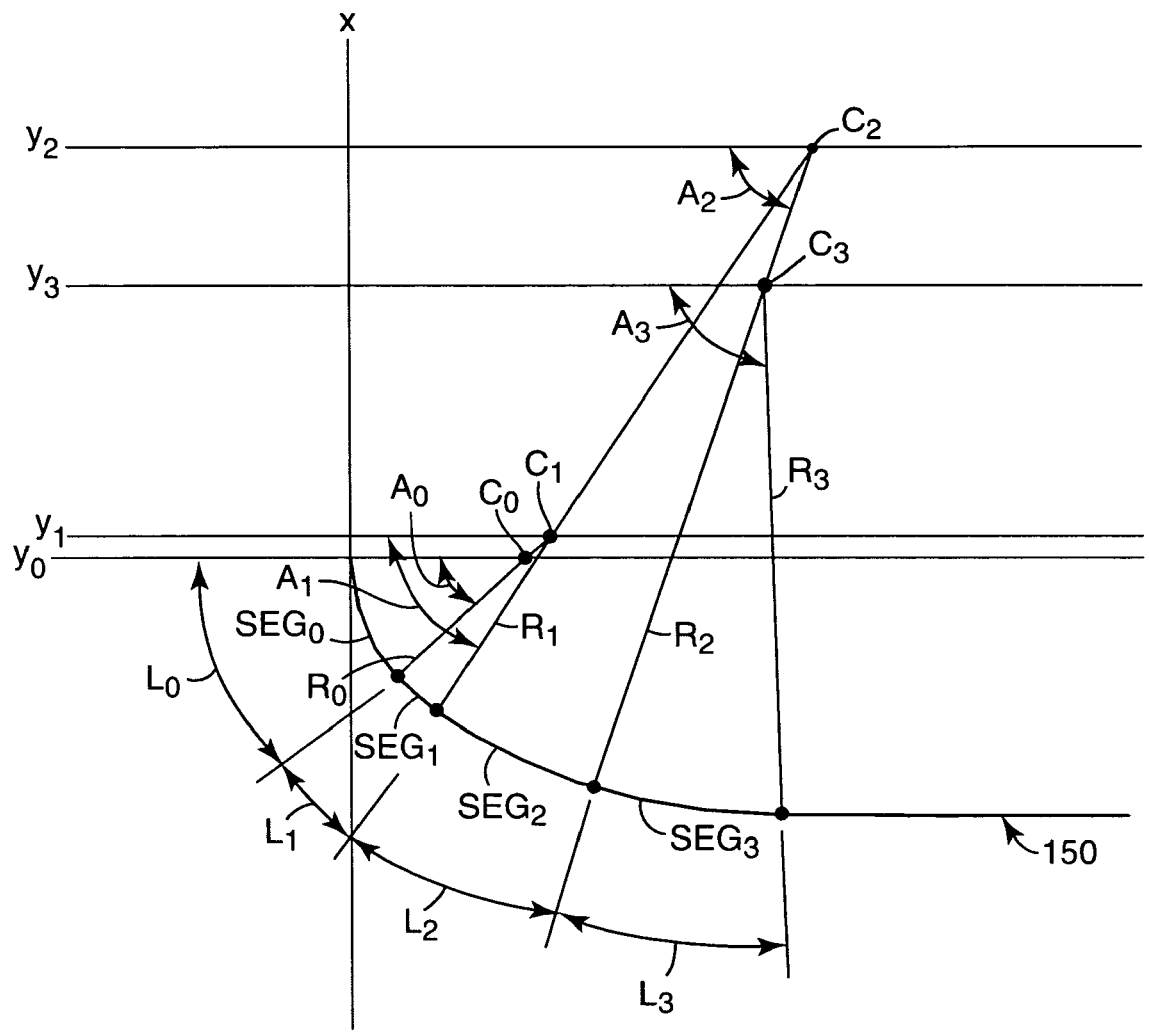

FIG. 3B is a diagram illustrating one exemplary virtual representation of one half of an archwire 150. In the example archwire of FIG. 3B, modeling software 20 represents each segment $SEG_i$ in the 3D virtual environment as a circular arc. Each circular segment $SEG_i$ is defined by a certain geometric relationship and corresponding geometric parameters. Object movement control module 24 uses these geometric parameters of the archwire 150 when moving an orthodontic object along archwire 150.

For example, each segment $SEG_i$ in FIG. 3B is a segment of a circle defined by points $C_i$ and corresponding radii $R_i$. These points $C_i$ and corresponding radii $R_i$ may be defined and provided by the archwire manufacturer or may be determined by the system. The points $C_i$ correspond to the centers of circles whose corresponding segments $SEG_i$ create a mathematical representation of archwire 150. Axes $y_i$ pass through the respective points $C_i$ and are parallel to the median line $y_0$ of archwire 150. End angles $A_i$ are defined as the angle radii $R_i$ makes with the corresponding axis $y_i$. In one embodiment, object movement control module 24 may determine end angles $A_i$ using the following equation:

$$A_i = \tan^{-1}(|C_{i+1,y} - C_{i,y}|/|C_{i+1,x} - C_{i,x}|).$$

Segment lengths $L_i$ are defined as the length of each segment $SEG_i$ that represent archwire 150. In other words, each segment length $L_i$ is defined as a fraction of the total circumference of the circle defined by $C_i$ and $R_i$ for the corresponding segment $SEG_i$. In one embodiment, object movement control module 24 may determine the length of each segment that makes up archwire 150 using the following equation:

$$L_i = 2\pi R_i * ((A_i - A_{i+1})/360).$$

Figure 3C:
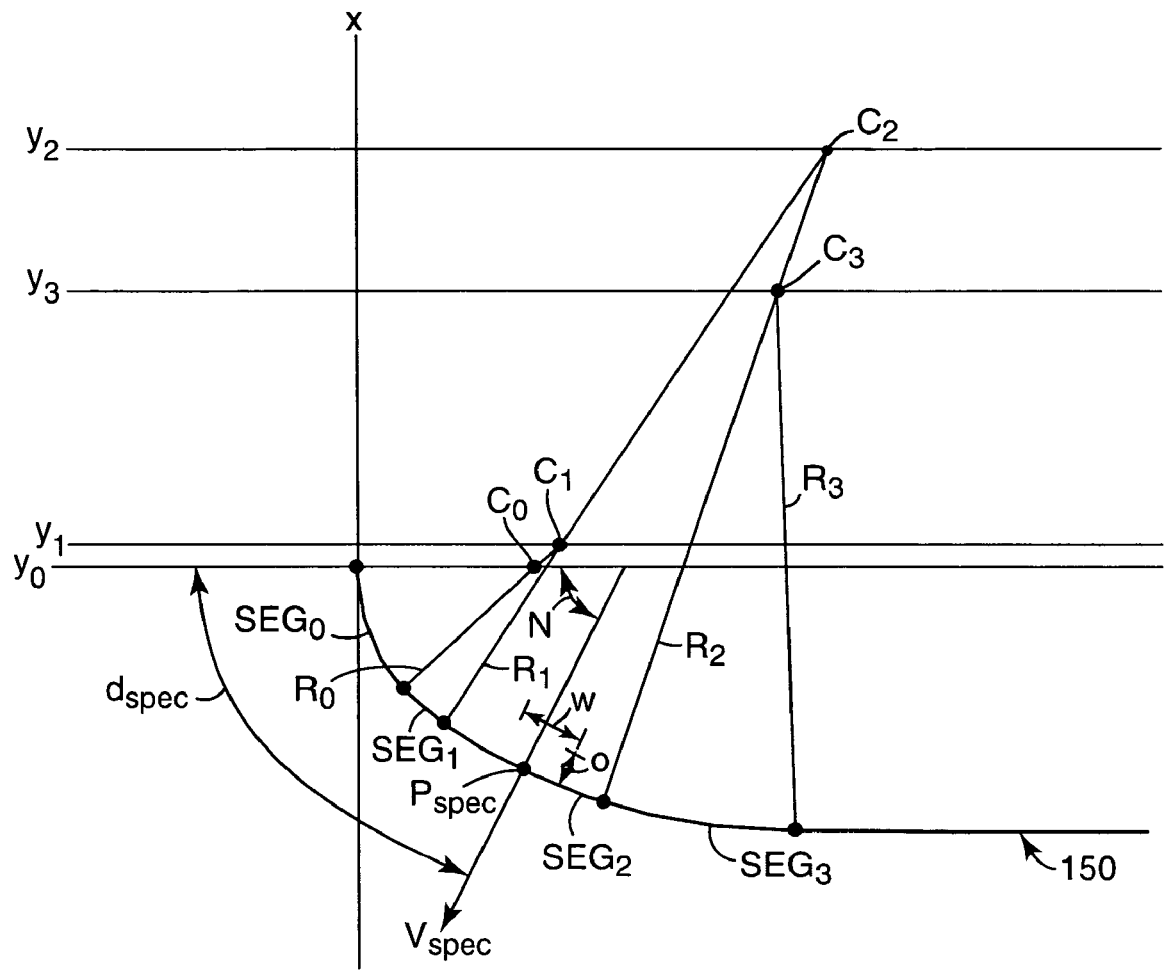

FIG. 3C is a diagram illustrating the exemplary virtual archwire of FIG. 3B and additional geometric parameters used by object movement control module to move an orthodontic object. The distance $d_{spec}$ is measured along archwire 150 from the median line $y_0$ of archwire 150. The distance $d_{spec}$ corresponds to input indicative of a desired movement of the orthodontic object along the archwire 150. The desired movement may be obtained from treatment planning control module 28 or may be specified and input manually by orthodontic practitioner 8.

The coordinates of the point $P_{spec}$ are the calculated coordinates of the point on the archwire where the orthodontic object is to be placed in the 3D virtual environment. Vector $V_{spec}$ is the normal vector to the segment $SEG_i$ at the point $P_{spec}$. Angle N is the angle normal vector $V_{spec}$ makes with the y axis on segment $SEG_i$ where the point $P_{spec}$ is located. In one embodiment, object movement control module 24 may determine N using the following equations:

$$N = |d_{spec}|/R_i \text{ for } i=0, \text{ or}$$

$$N = A_{i+1} + (|d_{spec}| - \text{sum}(L_0 \ldots L_{i-1}))/R_i \text{ for } i>0.$$

The actual coordinates on the archwire corresponding to the desired movement of the orthodontic object, $P_{spec}$, may be determined using the following equations:

$$P_{spec}=(R_i*\sin(-N)+C_{i,x}, R_i*\cos(-N)+C_{i,y}) \text{ for } d\geq 0, \text{ or}$$

$$P_{spec}=(-(R_i*\sin(-N)+C_{i,x}), R_i*\cos(-N)+C_{i,y}) \text{ for } d<0.$$

A normal vector $V_{spec}$ at specified point $P_{spec}$ indicates is directed toward the labial side of the dental arch. In one embodiment, object movement control module 24 may determine normal vector $V_{spec}$ using the following equations:

$$V_{spec}=(\sin(-N), \cos(-N)) \text{ for } d\geq 0, \text{ or}$$

$$V_{spec}=(-\sin(-N), \cos(-N)) \text{ for } d<0.$$

Object movement control module 24 also determines an offset O based on the bracket slot width W. The bracket slot width W is a defined metric associated with an individual bracket. In one embodiment, object movement control module 24 may determine offset O using the following equation:

$$O=R_i-sqrt(R_i^2-(W/2)^2).$$

TABLE 1 presents the values for the example archwire 150 shown in FIGS. 3A and 3B. It shall be understood, however, that these values are for exemplary purposes only, and that many other representations of an archwire could also be used without departing from the scope of the present invention. For example, although the archwire shown in FIGS. 3A and 3B is represented by four circular segments, the archwire could be represented using a greater or lesser number of segments, and also by other non-circular geometric relationships. The invention is therefore not limited to any particular number of segments or the any particular equations by which the archwire parameters are determined.

TABLE 1

|  | $SEG_0$ | $SEG_1$ | $SEG_2$ | $SEG_3$ |
| --- | --- | --- | --- | --- |
| $C_i$ | (0.8835, 0.0) | (0.9976, 0.1056) | (2.3035, 2.0567) | (2.0664, 1.3710) |
| $R_i$ | 0.8835 | 1.0390 | 3.3862 | 2.6610 |
| $A_i$ | 42.78 | 56.23 | 71.00 | 90.00 |
| $L_i$ | 0.6597 | 0.2439 | 0.8729 | 0.8824 |

Figure 4:
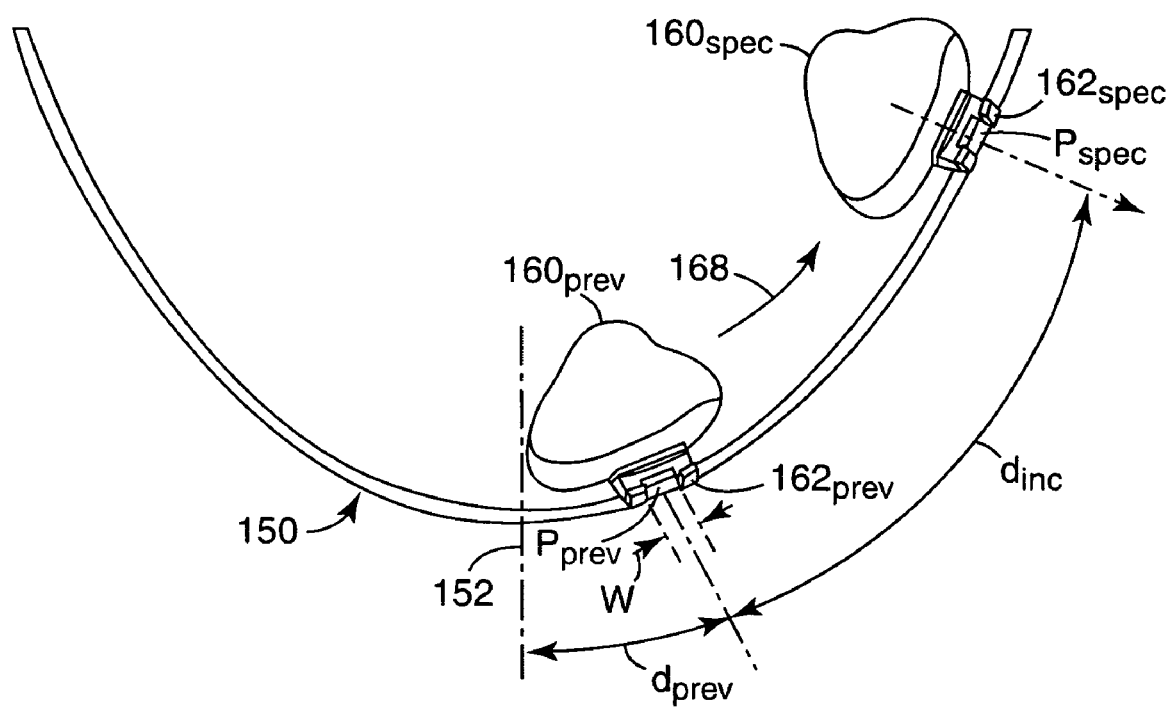
FIG. 4 illustrates movement of an orthodontic appliance and its associated tooth along an archwire.

FIG. 4 illustrates movement of an orthodontic object, namely orthodontic appliance 162 and its associated tooth 160, along an archwire 150. In this embodiment, both the tooth 160 and the bracket 162 are shown. In another embodiment, either the bracket 162 or the tooth 160 may be shown alone. In another embodiment, a portion of the tooth 160 may be shown, either alone or in combination with bracket 162. In another embodiment, bracket 162 may be represented by a crosshair or other manner of illustrating position of a bracket.

In the example of FIG. 4, object movement control module 24 moves bracket 162 and its associated tooth 160 in the direction indicated by arrow 168 from its previous coordinates $P_{prev}$ to new coordinates $P_{spec}$. In one embodiment, practitioner 8 may interact with user interface 22 to move the tooth and/or the bracket 162. For example, practitioner 8 may click and drag either the tooth and/or the bracket (or other orthodontic object) to indicate desired movements of the orthodontic object along archwire 150. In this example, modeling software 20 may be configured such that incremental movements of a mouse or other peripheral device correspond to defined movements of the selected orthodontic object along archwire 150. For example, incremental movements of a mouse or other peripheral device may correspond to movement of an orthodontic object along the archwire by a defined distance $d_{inc}$. Alternatively, practitioner 8 may manually input data indicative of desired movements of the orthodontic object by, for example, specifying $d_{inc}$ as a defined distance from an adjacent orthodontic object. In another embodiment, the distance $d_{spec}$ may be computed automatically, for example, by treatment planning control module 28 during the course of an interactive treatment planning session.

To determine the new coordinates of position $P_{spec}$, object movement control module first calculates the distance $d_{spec}$. The distance $d_{spec}$ may be obtained by adding the previous distance $d_{prev}$ to the distance $d_{inc}$.

Object movement control module 24 moves the selected orthodontic object, in this case bracket 162 and/or tooth 160, along archwire 150 in a manner that is constrained by the defined geometries of the segments associated with the archwire. Moreover, object movement control module 24 seamlessly moves bracket 152 and/or tooth 160 as the bracket and tooth traverse the defined segments.

Figure 5:
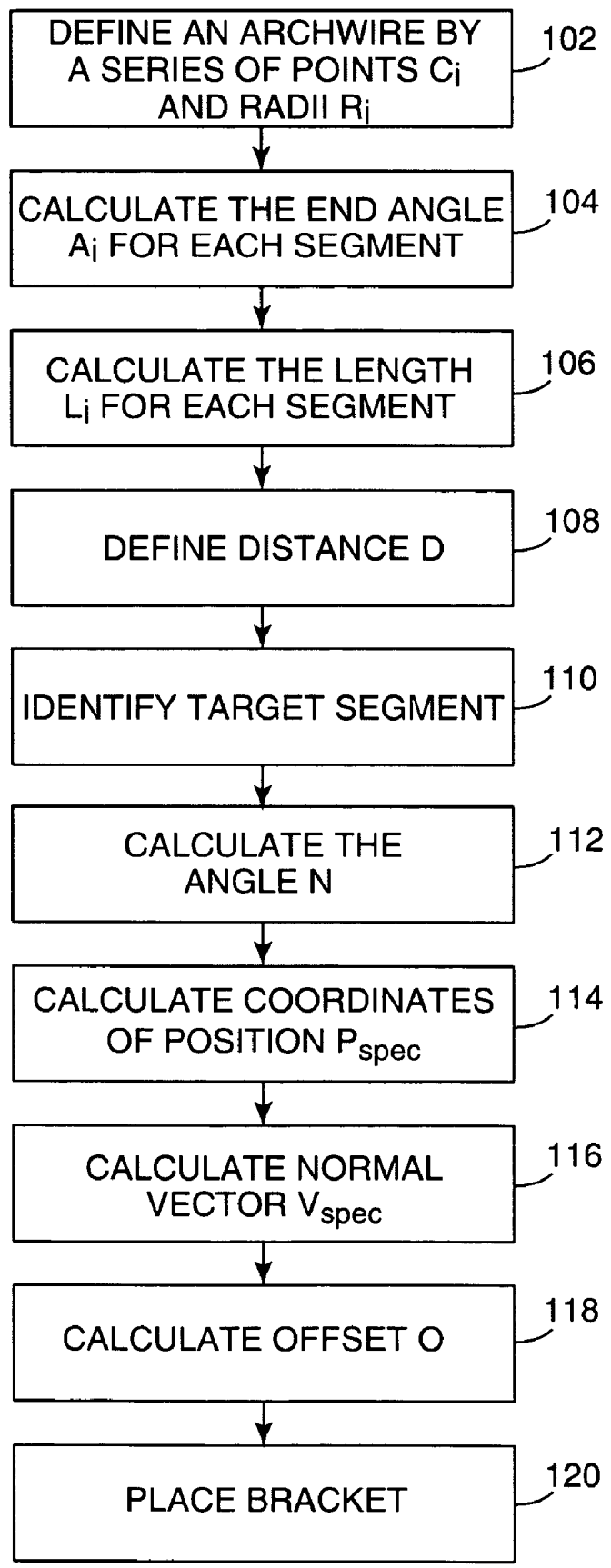
FIG. 5 is a flowchart illustrating exemplary operation of modeling software executing on the client computer device to move teeth along an archwire.

FIG. 5 is a flowchart illustrating exemplary operation of object movement control module 24 executing on client computer device 4 to move an orthodontic object along an archwire within the 3D environment in accordance with inputs indicative of desired movement of that orthodontic object. More specifically, the flowchart of FIG. 5 illustrates operation of object movement control module 24 in moving a selected orthodontic object along a virtual archwire defined by a series of points determined based on the radii and centers of circles whose segments represent an archwire as described above with respect to FIG. 3. It shall be understood, however, that although the flowchart of FIG. 5 is specific to circular segments, other geometric relationships for the segments could also be used in the flowchart of FIG. 5 without departing from the scope of the present invention.

Initially, object movement control module 24 defines the archwire by a series of points $C_i$ and corresponding radii $R_i$ (102). These values may be defined by the archwire manufacturer, practitioner or other source. Object movement control module 24 calculates the end angles $A_i$ (104) and the segment lengths $L_i$ (106) for each segment. Object movement control module 24 receives the input concerning the desired movement of the orthodontic object (108). For example, this input may include input from the practitioner or from other software modules corresponding to the distance $d_{inc}$ (see FIG. 4) that the orthodontic object is to be moved along the archwire.

Object movement control module 24 identifies which segment $SEG_i$ is located using the segment lengths $L_i$ (110). For example, the appropriate segment $SEG_i$ may be identified by comparing the distance $d_{spec}$ to the segment lengths $L_i$. The appropriate segment $SEG_i$ is identified when the distance $d_{spec}$ lies within the boundaries of the corresponding segment length $L_i$.

Object movement control module 24 next calculates the angle N on the identified segment $SEG_i$ (112). Object movement control module can then calculate the coordinates of the point on the archwire, $P_{spec}$, to which the orthodontic object is to be moved (114). Object movement control module 24 also calculates the normal vector $V_{spec}$ (116), and the offset O (118) at point $P_{spec}$. Finally, object movement control module 24 places the orthodontic object at specified point $P_{spec}$, offset O, along the virtual archwire (120). In particular, object movement control module 24 translates an origin associated with the orthodontic object to the specified point $P_{spec}$ based on the computed normal vector $V_{spec}$ and the offset O.

Figure 6A:
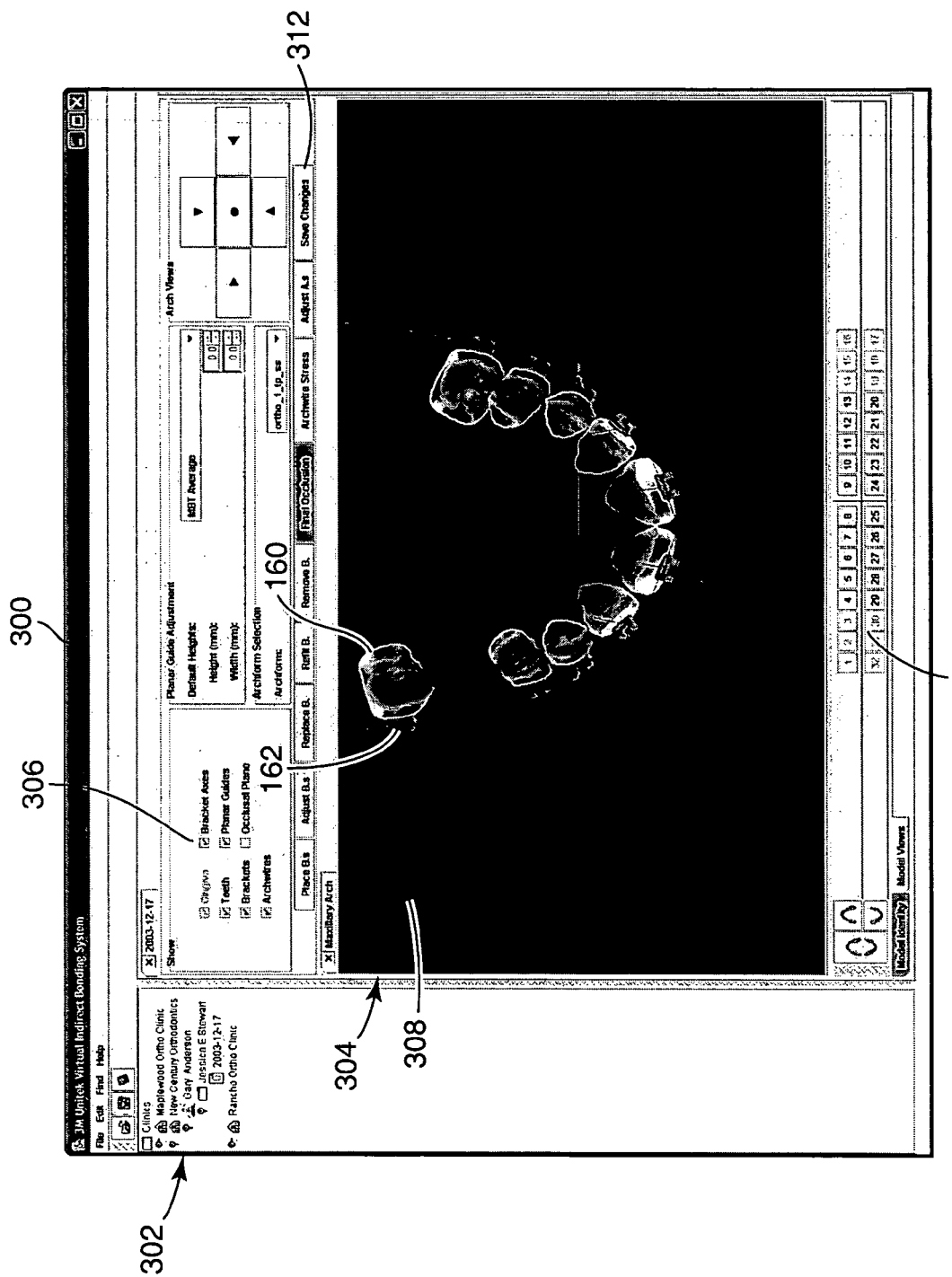
FIGS. 6A and 6B are display diagrams of an exemplary user interface presented by the modeling software.
Figure 6B:
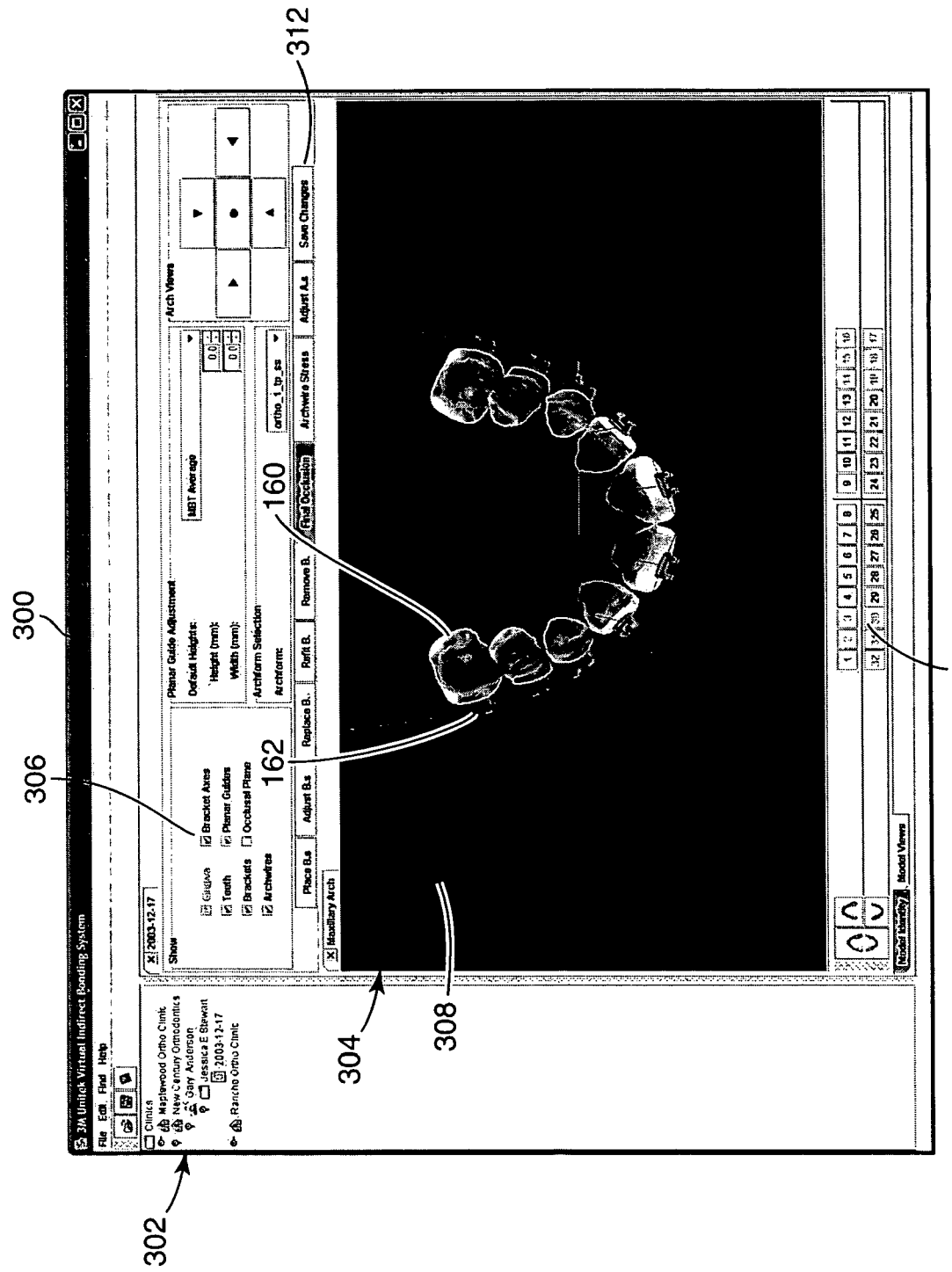

FIGS. 6A and 6B are display diagrams illustrating an exemplary graphical user interface (GUI) presented by modeling software 20. For example, FIGS. 6A and 6B illustrate an exemplary user interface 300 that depicts the movement of an orthodontic object, in this case tooth 160 and bracket 162, from one position to another position along an archwire.

User interface 300 allows a practitioner to choose from any of several views of the patient's dentition. For example, in one view, user interface 300 may display an entire arch (as shown in FIGS. 6A and 6B). In other views, user interface may display specified portions of a patient's dental arch, or may display one or more individual teeth, portions of a tooth or teeth, or one or more appliances or representations of appliances as may be selected by the practitioner 8.

Treatment planning control module 28 (see FIG. 2) enables practitioner 8 to interactively develop a treatment plan and corresponding orthodontic prescription which will result in a desired functional final occlusion using the virtual three-dimensional model of the patient's dentition presented on user interface 300. The user interface 300 may present the crowns and/or the roots or gingiva of the teeth to the practitioner 8 for visualization and interactive movement of the teeth. The virtual orthodontic objects may be moved independently in three dimensions. The orthodontic objects may be an entire orthodontic arch, specified groups of teeth and/or appliances, roots or gingiva, or individual orthodontic appliances, or individual teeth.

In the illustrated embodiment of FIG. 6A, user interface 300 includes a menu input area 302 by which a user, e.g., practitioner 8, may access patient data 306 for a particular patient 6. User interface 300 further includes display area 304 for presenting the 3D rendered representation of the teeth of patient 6. In the example of FIG. 6A, display area 304 presents a virtualized top view 308 of the dental arch of patient 6 in which tooth 160 is not yet in position with respect to the rest of the teeth in the dental arch. In the example of FIG. 6B, display area 304 presents a virtualized top view 310 of the dental arch of patient 6 after object movement control module 24 has moved tooth 160 along the archwire to a specified position.

User interface 300 provides selection mechanism 306 by which practitioner 8 can selectively enable and disable the rendering and display of any of several different views of the patient's dental arch within the display area 302. User interface 300 includes navigation tools 306, 310, and 312, for example, which may include typed commands, icons and/or graphical devices superimposed on the displayed model, that enable a user to manipulate the model on the display and simulate the movement of specified orthodontic objects or groups of orthodontic objects in the model relative to other orthodontic objects in the model in the 3D environment.

User interface also allows practitioner 8 to specify the desired movement or placement of orthodontic objects by, for example, manual input of desired metrics or measurements of the orthodontic objects such as brackets or teeth with respect to each other or with respect to other brackets or teeth in the dentition, pointing and clicking a mouse or other peripheral device on the desired orthodontic object, or specifying the location of the orthodontic object. For example, the practitioner may specify a position at which tooth 160 is to be placed by clicking and dragging a tooth 160 or a bracket 162 to a specified point on the virtual archwire, by manually entering a metric indicative of the desired point on the virtual archwire, by specifying a distance from an adjacent tooth or bracket, etc.

The new position may also be determined automatically. For example, the specified positions may be determined automatically by treatment planning control module 28 as part of an automated or interactive treatment planning session. In one example, client computing device 4 may be configured to automatically place teeth along the archwire based on a proposed orthodontic prescription to generate a final occlusion that may result from that proposed prescription. Such a system is described in copending and commonly assigned patent U.S. patent application Ser. No. 10/959,624, entitled, "Placing Teeth Along an Archwire Within a Three-Dimensional (3D) Environment", to Raby, et al., filed on even date herewith, which is incorporated herein by reference in its entirety. As another example, client computing device 4 may be configured to allow practitioner to specify desired positions of an orthodontic appliance on a tooth. Such as system is described in the above-mentioned copending and commonly assigned U.S. patent application Ser. No. 10/903,686, entitled "Automatic Adjustment of an Orthodontic Bracket to a Desired Occlusal Height Within a Three-Dimensional (3D) Environment", to Raby et al., filed on Jul. 30, 2004, which is incorporated herein by reference in its entirety.

Figure 7A:
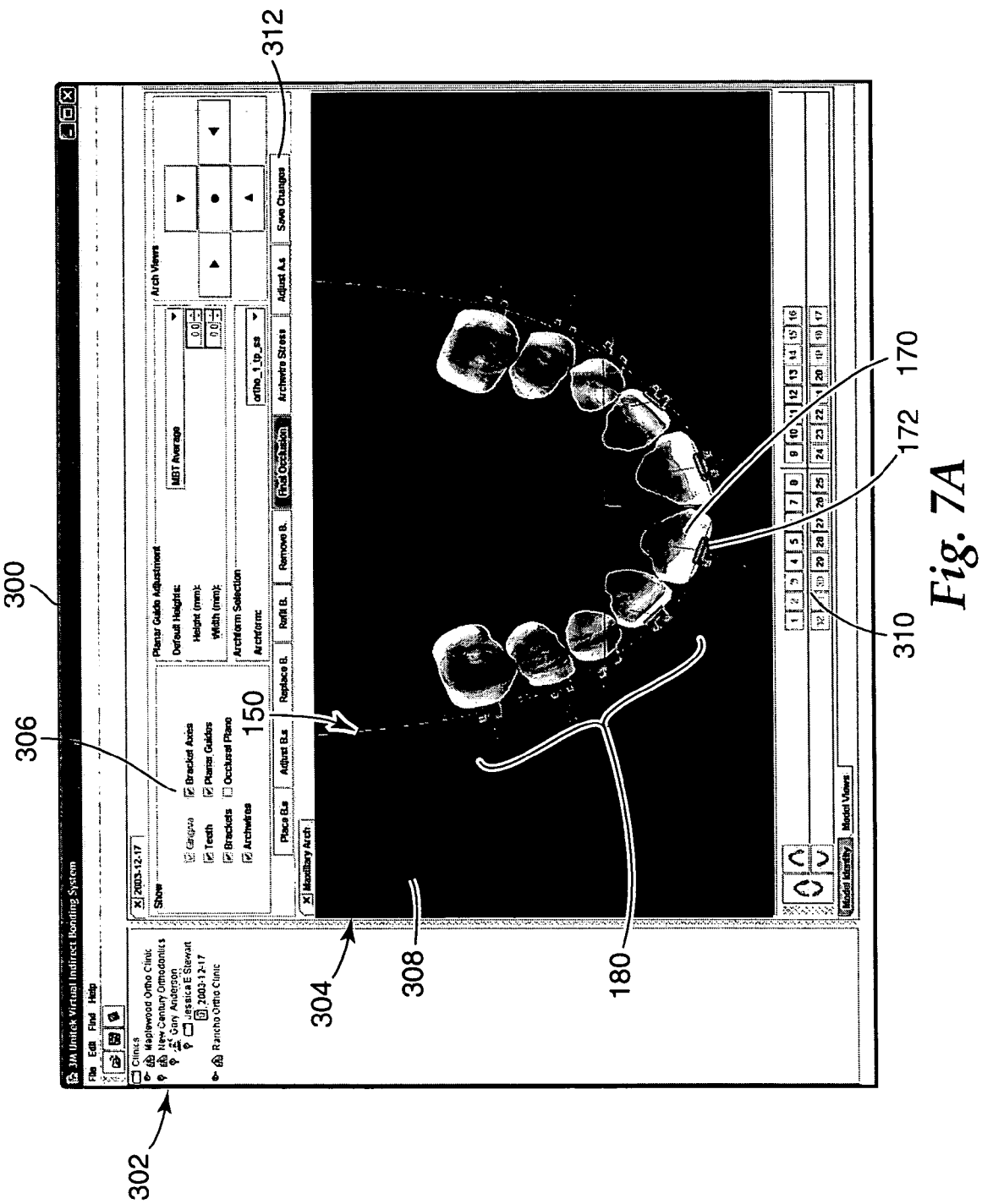
FIGS. 7A and 7B are display diagrams of an exemplary user interface presented by the modeling software.
Figure 7B:
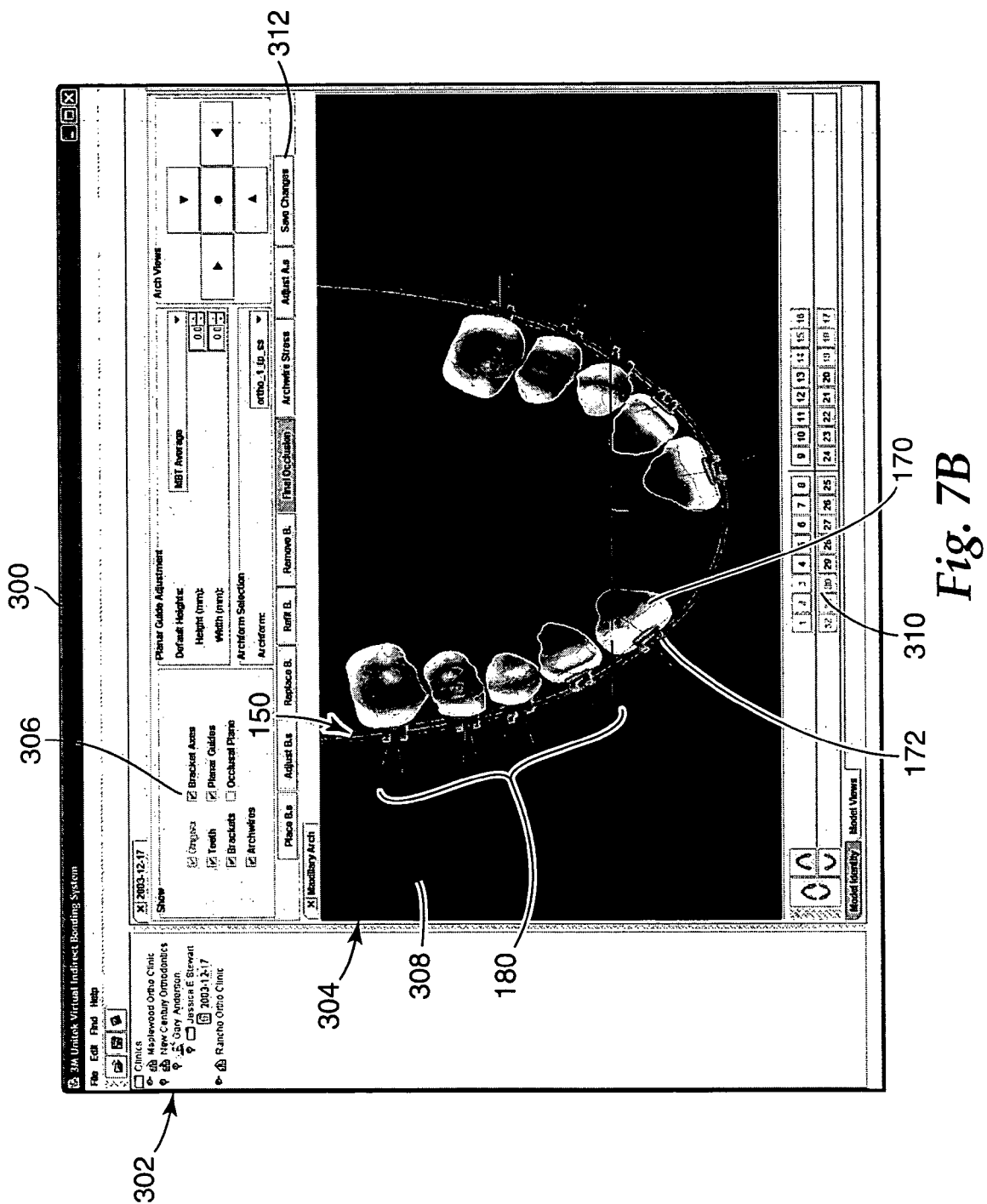

FIGS. 7A and 7B are display diagrams illustrating an exemplary graphical user interface (GUI) presented by modeling software 20. FIGS. 7A and 7B illustrate an exemplary user interface 300 that depicts the movement of a tooth 170 from one position to a specified position along an archwire 150 performed by object movement control module 24. FIGS. 7A and 7B also depict the movement of other affected teeth 180 to corresponding new positions along the archwire 150 resulting from movement of tooth 170. Object movement control module 24 therefore identifies and automatically moves affected orthodontic objects in the dentition that necessarily must move as a consequence of moving the target bracket to the specified position. In one embodiment, this feature may be enabled or disabled by the practitioner as desired thru interaction with user interface 22.

Object movement control module 24 automatically moves the affected orthodontic objects 180 such that relative positions between adjacent orthodontic objects, such as brackets and/or teeth, are maintained. In the example of FIGS. 7A and 7B, for example, practitioner 8 may wish to move anterior-most tooth 170 from its previous position shown in FIG. 7A to a specified position of FIG. 7B. All affected teeth 180 (in this case, the teeth that are anterior to tooth 170) are also moved a corresponding amount to maintain the distance between adjacent teeth. Similarly, movement of any other orthodontic object specified by the system or by the practitioner may result in appropriate movement of other affected orthodontic objects such that previously determined distances between adjacent teeth are maintained.

Various embodiments of the invention have been described. These and other embodiments are within the scope of the following claims.

The invention claimed is:

1. A method comprising:
    representing an archwire within a three-dimensional (3D) environment with a plurality of segments;
    receiving input indicative of movement of an orthodontic object along the archwire; and moving the orthodontic object within the 3D environment as indicated along the archwire based on the plurality of segments.

2. The method of claim 1, further comprising displaying a digital representation of the orthodontic object.

3. The method of claim 1, further comprising:
defining each of the plurality of segments by a geometric relationship; and
moving the orthodontic object along the archwire based on the defined geometric relationships of the segments.

4. The method of claim 3, wherein the geometric relationship is a geometric curve.

5. The method of claim 4 wherein the geometric curve is a circular curve, a parabolic curve, an elliptical curve, a catenary curve, a second order curve, a third order curve, a cubic spline curve, or a parametric cubic curve.

6. The method of claim 3, wherein the geometric relationship is a linear relationship.

7. The method of claim 1, wherein the plurality of segments lie in a plane.

8. The method of claim 1, wherein the plurality of segments bend in three dimensions.

9. The method of claim 1, wherein moving the orthodontic object as indicated comprises determining on which of the plurality of segments a specified position is located based on the geometric relationships that define the plurality of segments.

10. The method of claim 1, wherein the orthodontic object is an orthodontic appliance, and further comprising associating a tooth with the orthodontic appliance and moving the tooth along with the orthodontic appliance.

11. The method of claim 1, wherein the orthodontic objects comprises an orthodontic appliance or a tooth.

12. The method of claim 11, wherein the orthodontic appliance comprises an orthodontic bracket, a buccal tube, a sheath, or a button.

13. The method of claim 1, further comprising receiving the input indicative of movement from a practitioner via a user interface.

14. The method of claim 13, wherein the practitioner interacts with the user interface by clicking and dragging the orthodontic object along the archwire.

15. The method of claim 1, further comprising receiving the input indicative of movement from a treatment planning control module.

16. The method of claim 1, wherein each of the plurality of segments is represented by a circular curve, and wherein each circular curve is defined by a center and a radius.

17. The method of claim 16, wherein moving the orthodontic object as indicated comprises determining on which of the plurality of segments a specified position is located based on the centers and the radii that define the plurality of segments.

18. The method of claim 1, wherein a proposed orthodontic prescription includes a plurality of orthodontic appliances each associated with a different one of a plurality of teeth in a dental arch and wherein the archwire is received in a slot of each orthodontic appliance.

19. The method of claim 1, further comprising automatically moving affected orthodontic objects along the archwire as a consequence of moving the orthodontic object as indicated.

20. The method of claim 19, wherein the affected objects are automatically moved such that relative positions between adjacent orthodontic objects are maintained.

21. A system comprising:
a computing device; and
modeling software executing on the computing device, wherein the modeling software comprises:
an object movement control module that represents an archwire within a three-dimensional (3D) environment with a plurality of segments;
receives input indicative of movement of an orthodontic object along the archwire; and
moves the orthodontic object as indicated along the archwire based on the plurality of segments.

22. The system of claim 21, further comprising a user interface to display the orthodontic object within the 3D environment.

23. The system of claim 22, wherein the orthodontic object comprises an orthodontic appliance or a tooth.

24. The system of claim 23 wherein the orthodontic appliance comprises an orthodontic bracket, a buccal tube, a sheath, or a button.

25. The system of claim 21, wherein each of the plurality of segments is defined by a geometric relationship.

26. The system of claim 25, wherein the geometric relationship is a non-linear relationship.

27. The system of claim 26, wherein the non-linear relationship is a circular curve, a parabolic curve, an elliptical curve, a catenary curve, a second order curve, a third order curve, a cubic spline curve, or a parametric cubic curve.

28. The system of claim 25, wherein the geometric relationship is a linear relationship.

29. The system of claim 21, wherein the plurality of segments lie in a plane.

30. The system of claim 21, wherein the plurality of segments bend in three dimensions.

31. The system of claim 21, wherein moving the orthodontic object as indicated comprises determining on which of the plurality of segments a specified position is located based on the geometric relationships that define the plurality of segments.

32. The system of claim 21, wherein the orthodontic object is an orthodontic appliance, and further comprising associating a tooth with the orthodontic appliance and moving the tooth along with the orthodontic appliance.

33. The system of claim 21, wherein the object movement control module receives the indicated movement from a treatment planning control module.

34. The system of claim 21, wherein each of the plurality of segments is represented by a circular curve, and wherein each circular curve is defined by a center and a radius.

35. The system of claim 34, wherein the object movement control module further determines on which of the plurality of segments a specified position is located based on the centers and the radii that define the plurality of segments.

36. The system of claim 21, wherein the object movement control module further automatically moves affected orthodontic objects along the archwire as a consequence of moving the orthodontic object as indicated.

37. The system of claim 36, wherein the object movement control module automatically moves the affected orthodontic objects such that relative positions between adjacent orthodontic objects are maintained.

38. The system of claim 21, further comprising a database to store a library of virtual representations of archwires.

39. The system of claim 38, wherein the database is located remote from the computing device and coupled to the computing device via a network.

40. The system of claim 21, further comprising a user interface that receives input from the practitioner regarding the indicated movements.

41. A computer-readable medium comprising instructions for causing a programmable processor to:
represent an archwire within a three-dimensional (3D) environment with a plurality of segments;
receive input indicative of movement of an orthodontic object along the archwire; and
move the orthodontic object as indicated along the archwire based on the plurality of segments.

42. The computer-readable medium of claim 41, wherein the instructions cause the processor to define each of the plurality of segments with a geometric relationship.

43. The computer-readable medium of claim 41, wherein the instructions cause the processor to display the orthodontic object at the specified position within the 3D environment.

44. The computer-readable medium of claim 41, wherein the instructions cause the processor to determine on which of the plurality of segments a specified position is located based on the geometric relationships that define the plurality of segments.

45. The computer-readable medium of claim 41, wherein the instructions cause the processor to automatically move affected orthodontic objects along the archwire as a consequence of moving the orthodontic object as indicated such that relative positions between adjacent orthodontic objects are maintained.

* * * * *